United States Patent [19]
Ledis et al.

[11] Patent Number: 4,751,179
[45] Date of Patent: Jun. 14, 1988

[54] METHOD AND REAGENTS FOR DIFFERENTIAL DETERMINATION OF FOUR POPULATIONS OF LEUKOCYTES IN BLOOD

[75] Inventors: Stephen L. Ledis, Hialeah; Harold R. Crews, Pembroke Pines; Ted Sena, Miami, all of Fla.

[73] Assignee: Coulter Electronics, Inc., Hialeah, Fla.

[21] Appl. No.: 615,966

[22] Filed: May 31, 1984

[51] Int. Cl.$^4$ .......... C12Q 1/04; C12Q 1/06; G01N 1/00; G01N 33/48

[52] U.S. Cl. ................. 435/34; 435/39; 424/3; 436/10; 436/17; 356/36

[58] Field of Search ............ 436/63, 10, 17; 435/2, 435/29, 30, 34, 39; 424/3, 7.1; 356/36, 39; 252/408.1

[56] References Cited

U.S. PATENT DOCUMENTS

| | | | |
|---|---|---|---|
| 2,656,508 | 10/1953 | Coulter | 324/71 |
| 3,259,842 | 7/1966 | Coulter et al. | 324/71 |
| 3,446,751 | 5/1969 | Weichselbaum | 424/3 X |
| 3,502,974 | 3/1976 | Coulter et al. | 324/71 |
| 3,710,933 | 1/1973 | Fulwyler et al. | 424/7.1 X |
| 3,741,875 | 6/1973 | Ansley et al. | 195/103.5 R |
| 3,836,849 | 9/1974 | Coulter et al. | 324/71 |
| 3,873,467 | 3/1975 | Hunt | 436/10 |
| 3,883,247 | 5/1975 | Adams | 356/39 |
| 3,884,579 | 5/1975 | Mauthner | 436/63 X |
| 4,099,917 | 7/1978 | Kim | 23/230 B |
| 4,146,604 | 3/1979 | Kleinerman | 424/3 |
| 4,198,206 | 4/1980 | Ryan | 436/17 X |
| 4,213,876 | 7/1980 | Crews et al. | 436/10 X |
| 4,286,963 | 9/1981 | Ledis et al. | 23/230 B |
| 4,485,175 | 11/1984 | Ledis et al. | 436/63 |
| 4,492,752 | 1/1985 | Hoffman et al. | 424/3 X |
| 4,500,509 | 2/1985 | Kass | 424/7.1 X |
| 4,506,018 | 3/1985 | North, Jr. | 436/10 |
| 4,521,518 | 6/1985 | Carter et al. | 436/63 X |

OTHER PUBLICATIONS

Hawley, The Condensed Chemical Dictionary, Tenth Edit., New York, Van Nostrand Reinhold, (1981), p. 959.
Hughes-Jones, J. Clin. Path, vol. 27, p. 623 (1974).
Ornstein, Blood Cells, vol. 25, p. 57 (1976).
Humphries et al., Ser. Haemt, vol. V-2, p. 142 (1972).
Ladinsky, Cancer Res., vol. 27, p. 1689, (1967).
Van Dilla, Proc. Soc. Exp. Biol. (N.Y.) vol. 125, p. 367 (1967).
Leif et al., Clinical Chemistry, vol. 23, pp. 1492-1498 (1977).
Thomas et al., J. Histochemistry and Cytochemistry, vol. 25, No. 77, pp. 827-835 (1977).
Ansley et al., Adv. Automated Anal., vol. 1, p. 437 (1971).
Kaplow, Macrophages and Lymphocytes, Part A, 211 Plenum (1980).
Sims, Biochem. 13 3315 (1974).
Salzman et al., Acta Cytologya, vol. 19, No. 4, pp. 374-377 (1979).
Taber's Cyclopedic Medical Dictionary, 8th Edit. F. A. Davis Company, Philadelphia.
Dorland's Illustrated Medical Dictionary, 24th Edit., W. B. Saunders Co., Philadelphia.
Stedman's Medical Dictionary, Williams & Wilkins Company Baltimore.

Primary Examiner—Robert J. Warden
Assistant Examiner—Randall E. Deck
Attorney, Agent, or Firm—Meredith P. Sparks; Gerald R. Hibnick

[57] ABSTRACT

This invention describes a reagent system, including saponin in a lysing reagent and a rapidly active cross-linking agent such as glutaraldehyde as a fixing reagent, which reproducably affects whole blood to cause the red blood cells to stromatolyze and modifies the leukocytes to generate data to define four distinct clusters for detection and classification by flow analysis instrumentation. The clusters represent the four major leukocyte types found in blood: lymphocytes, monocytes, neutrophils and eosinophils, thus providing a method of leukocyte differential analysis. The parameters used for the leukocyte classification include combinations of two or more of DC (Coulter) volume, high frequency (RF) size, opacity (RF size/DC volume), light scatter at various angular ranges, and fluorescence at various wavelengths of illumination.

8 Claims, 1 Drawing Sheet

METHOD AND REAGENTS FOR DIFFERENTIAL DETERMINATION OF FOUR POPULATIONS OF LEUKOCYTES IN BLOOD

BACKGROUND OF THE INVENTION

Many methods have been used for removing the red blood cells from whole blood so that the leukocytes can be studied by flow techniques. Physical separation by sedimentation or centrifugation or density gradients, aggregation of red blood cells and other physical techniques are useful for research purposes, but are too slow and difficult for automated clinical analysis of leukocytes. Quaternary ammonium salt detergents are very efficient lytic agents, but have been found to be too damaging to the leukocytes, resulting at best, in only three clusters of leukocytes, by DC volume analysis, representing the lymphocytes, monocytes and granulocytes.

Kim, U.S. Pat. No. 4,099,917, 1978, describes a method of sensitizing red blood cells with a non-ionic detergent, adding a formaldehyde fixative, and incubating the blood at 58° C., to lyse the red blood cells selectively, leaving leukocytes and platelets intact for light scatter measurements. This process is rather slow, about three minutes, and may be sufficient to make the red blood cells transparent toward optical measurements, but not towards electronic measurements, which require more thorough stromatolyzing of the red blood cells. The same is true of other lytic procedures, such as hypotonic lysis, ammonium chloride lysis, and ethylene or propylene glycol treatment which render the red blood cells transparent towards optical, i.e. light scatter, fluorescence measurements, but not towards electronic, i.e. DC volume and R.F. volume parameters.

The natural product known as saponin has long been used as a red blood cell lytic agent. Saponin is chemically defined as a class of glycosides of various mono- or polysaccharides, with steroid or triterpene alcohols. Quillaja saponin is isolated as a natural product from quillaja tree bark. This saponin has detergent-like properties and hemolyzes red blood cells when used at very low concentrations compared to synthetic ionic and nonionic hemolytic agents. However, the chemical treatment, structure and purity of commercial quillaja saponin is not generally specified or tested, and the material does vary from lot to lot.

The activity of saponin is more selective towards red blood cells than are the quaternary ammonium salt detergents. Unfortunately, by employing lysing procedures known heretofore, it has not been possible to obtain leukocytes free from red blood cells, without doing some concomitant damage to the leukocytes.

Several reports describe the use of saponin with a second reagent which retards the leukocyte damage. Hughes-Jones, *J. Clin. Path.*, Vol. 27, page 623 (1974), reported a treatment of diluted whole blood with a saponin solution, followed in three minutes by treatment with serum which quenches the saponin activity. A direct current volume analysis was done on the leukocytes. Ornstein, *Blood Cells*, Vol. 25, page 57 (1967), used a solution of saponin, formaldehyde and other components, for twenty seconds followed by enzyme staining for detecting various leukocyte types. Humphries et al, *Ser. Haemat.* Vol. V-2, page 142 (1972), treat diluted whole blood with saponin, followed in thirty seconds with dilution in cold phosphate buffered saline to quench the lytic action. Other reports are Ladinsky, *Cancer Res.*, Vol. 27, page 1689 (1967), and Van Dilla, *Proc. Soc. Exp. Biol.* (NY), Vol. 125, page 367 (1967).

Commercial equipment employing the teachings of U.S. Pat. Nos. 2,656,508; and 3,259,842 are known under the trademark COULTER COUNTER ®, and the principle of their operation is commonly known as the Coulter principle.

According to the Coulter principle, first patented in U.S. Pat. No. 2,656,508, 1953, where a particle of microscopic size is passed through an electrical field of small dimensions of an order approaching those of a particle, there will be a momentary change in the electric impedance. If the electrical field is excited by a direct (DC) or low frequency current, the electrical change is closely proportional to the volume of the particle. In commercial apparatus, the changes are detected by some suitable means and used to operate counters and analyzers. The analyzers associated with such apparatus classify and size particles into populations based upon particle volume and record the data obtained.

The invention was materially expanded in U.S. Pat. No. 3,502,974, Coulter et al, 1970, using radio frequency (RF) current in addition to DC current field excitation to provide not only DC volume information concerning the particle studied, but also information due to the composition and nature of the material constituting the particle. This patent discloses apparatus capable of distinguishing between particles of identical size, but of different material. By generating the particle sensing field by means of both a low frequency or direct current (DC) and radio frequency (RF) current excitation, two or more interrelated output signals can be derived from the passage of a single particle through the electrical field. This is due to the fact that, although the subject particles are nearly always insulators with respect to low frequency or direct current fields, they are capable of carrying or impeding radio frequency current differently from the surrounding electrolyte. This may be due to differences in the dielectric constant in the case of homogeneous particles, or to the sac-like structure in the case of blood cells which have, enclosed in an extremely thin membrane, contents having conductivities different from the electrolyte. Thus, while all the DC current goes around a blood cell, some of the RF current will go through it. The ease with which the RF current will go through a particle is a measure of what is termed its "electrical transparency", or simply "transparency", in analogy with light transmission; whereas, a particle's ability to impede RF current is termed its "opacity". In later publications, "opacity" is defined as the RF impedance divided by the DC impedance.

The relative electrical opacity of a particle becomes an identifying feature of the particle contents, and hence, its particle type for classification purposes. To the extent that different types of particles each possess a different opacity, the difference between them is detectable. However, significantly different particles can possess substantially the same opacity and such particles cannot be classified effectively in this manner. In U.S. Pat. No. 3,836,849, 1974, Coulter et al taught that it is possible to change selectively the opacity of particle types by treatment of the particles, so that detectable differences result.

Although red blood cells and white blood cells nominally have different sizes, their size ranges tend to overlap, or at least under certain conditions of health could overlap. Moreover the opacities of these two types of blood cells may also overlap.

U.S. Pat. No. 3,741,875, Ansley et al, June, 1973, describes a process for obtaining a differential white blood cell count. A cytological fixing agent, which is a monoaldehyde such as formaldehyde, is added to a blood sample. A hemolyzing agent then is added after the fixation step to cause the red blood cells to release their hemoglobin content into solution. Addition of a specific cytochemical substrate, chromogenic precipitating coupling reagent, and pH buffer causes deposition of an insoluble dye in a specific type of cell containing an immobilized enzyme. The solution containing the dyed blood cells then is passed through a photometric counter. Using different specific substrates for different enzymes contained in specific kinds of cells, absolute and relative counts of the different kinds of cells are obtained. The cytological fixing solution utilized only a monoaldehyde. Dialdehydes are stated to be unsuitable, since they cross-link and produce extracellular precipitates.

Starting with whole blood, it is necessary to hemolyze the red blood cells, since there is danger that coincident passage of two or more red cells through a photometric counting station could be mistaken for dyed white blood cells or abnormal cells. A preferred way to solve the problem is to hemolyze the red blood cells by addition of a reagent to the suspension of cells to cause the red blood cells to rupture and release their hemoglobin content into the solution.

Ledis et al, U.S. Pat. Nos. 4,286,963, 1981, teaches a method for two-volume analysis of leukocytes using a COULTER COUNTER analyzer which employs only DC field excitation instrumentation and quaternary ammonium salts as lysing agents.

Ledis et al, U.S. Pat. No. 4,485,175, 1984, to Coulter Electronics, Inc. concerns a method and reagent system for three-volume differential determination of lymphocyte, monocyte, and granulocyte populations of leukocytes, using quaternary ammonium salts as lysing agents and the COULTER COUNTER Model S Plus automated blood counter, which instrument employs only direct current field excitation.

Previous methods of flow analysis of leukocytes using DC volume, or light scatter at various angles have shown only three clusters of leukocytes, corresponding to lymphocytes, monocytes, and granulocytes including neutrophils and eosinophils. The eosinophils have been observed as a distinct cluster by using special fluorescence techniques.

Other dye compositions for differential analysis of white blood cells include a hypotonic aqueous solution of a metachromatic fluorochrome dye such as acridine orange, Adams, U.S. Pat. No. 3,883,247. The white cell analysis is made by suspending a sample of fresh blood in the dye solution, subjecting the suspension, before dye uptake equilibrium is reached, to radiation from a light source, e.g. radiation from a blue laser, having a wave length within the range of absorption of the dye, and distinguishing the white cells from other blood particles by detecting fluorescences, e.g. green vs. red fluorescences.

Fluorescent dyes suitable for specifically dyeing eosinophil granules are the anilino or toluidino naphthalene sulfonic acids and their alkyl, alkoxy or halogen substituted derivatives.

The development of instrumentation and fluorochromes for automated multiparameter analysis of cells is further described by R. C. Leif et al. in Clinical Chemistry, Vol. 23, pp 1492–98 (1977).

Eosinophils have been observed also by enzyme staining such as by the Technicon Hemalog D and H6000 instruments, (Ansley and Ornstein, Adv. Automated Anal., Vol. 1 437 (1971), Kaplow, Macrophages and Lymphocytes, Part A, 221 Plenum (1980).

The detection of populations of particular leukocytes, and the concurrent relationship of these populations to one another in a human blood sample is important in medical research and for the diagnosis of certain human diseases. Such data are useful as a screening tool for calling attention to abnormal leukocyte ratios. Abnormal situations identified by this method give information of diagnostic significance and alert the technologist to the need for further study.

SUMMARY OF THE INVENTION

This invention concerns a reagent system and a method for classifying and counting at least four populations of leukocytes using flow analysis instrumentation. More particularly, the present invention relates to a multicomponent reagent system for rapidly eliminating the red blood cells in a sample of whole blood and for maintaining and modifying leukocytes in a manner suitable for flow analysis classification into four major categories which have been identified as (1) lymphocytes, (2) monocytes, (3) neutrophils and (4) eosinophils.

The reagent system comprises aqueous solutions of: (A) a lytic diluent containing saponin; or a blood diluent which is followed by a lytic reagent containing saponin; (B) a fixing reagent containing a cross-linking compound such as glutaraldehyde, each of these two components being maintained at a predetermined concentration, pH and osmolality. This method is rapid, reliable and effective for normal and abnormal bloods and blood control material.

Preservatives can be added to inhibit the growth of microorganisms. Other additives also can be included. A fluorescent dye is included in the lytic diluent when studies make a determination by fluorescence.

The lysed and fixed blood sample is brought to the proper concentration for flow analysis using a diluent which also can contain potassium ferricyanide and potassium cyanide for converting the hemoglobin to a chromogen suitable for hemoglobinometry.

This invention relates also to a method for discriminating of major categories of leukocytes by flow instrumentation which measures two or more of the primary parameters of DC volume, RF size, fluorescence and light scatter, and also provides histograms based on selected mathematical combinations of the primary parameters.

DETAILED DESCRIPTION OF THE INVENTION

Figure 3:
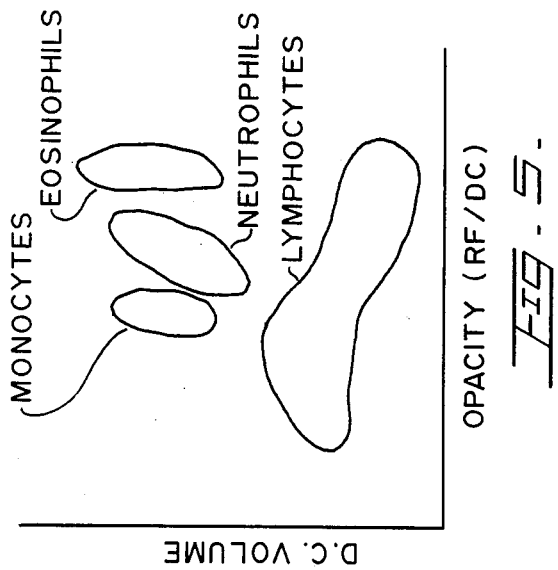
FIGS. 1 through 5 illustrate the leukocyte subpopulations identification accomplished by the method of this invention. In the diagrams of the FIGURES, the encircled areas represent cell populations or cell clusters that are generated by accumulation of data points, in which each data point is determined by coordinates which are proportional to certain cell parameters. This form of diagram is known as a cytogram. The hereinafter presented Examples explain each FIGURE.

The purpose of this invention is to provide a method for the rapid lysing of the red blood cells in whole blood in a manner that preserves and/or modifies the leukocytes, so that they can be distinguished or classified into subpopulations. In the present invention, whole blood is treated with a lysing reagent. This lysing reagent has two forms: (1) a lytic diluent containing saponin, which simultaneously functions to dilute the whole blood sample and stromatolyse its red blood cells; or (2) a two part system comprised of non-lytic blood diluent followed by a lytic reagent containing saponin. The lysing reagent is followed by treatment with a cross-linking fixing reagent which alters the white cells so that different white cell subpopulations are modified in order that the white cells can be distinguished and classified. In some embodiments, the flow analysis instrumentation utilizes radio frequency (RF) current as well as direct current (DC) field excitation for generating the measurement data. In other embodiments, optical detection is utilized without as well as with DC field excitation. The desired parameters can be measured directly, or by a mathematical calculation from the direct measurements.

FIGS. 1 through 5 are derived from cytograms obtained from normal blood samples. A cytogram is produced by a plurality of points or dots, wherein each dot represents a single cell, and the location of the dot is given by coordinates which are proportional to selected cell parameters; for example, the right angle and forward light scatter intensities produced by the cell in the instrument. In this manner, four clusters of dots or cells are formed, and their areas are encircled in FIGS. 1 through 5 and all of which are identified as leukocytes, namely (1) lymphocytes, (2) monocytes, (3) neutrophils and (4) eosinophils, are the four major categories of leukocytes.

Because a high concentration of saponin is needed to provide rapid stromatolyzing of the red cells, it must be used with a rapidly active cross-linking fixing reagent in order to protect the leukocytes agaibst damage. Slow acting monoaldehydes, such as formaldehyde, are ineffective for preserving the leukocytes in this reaction. When saponin alone is added in amounts just barely sufficient to stromatolyse the red blood cells, it requires much too long, about twenty minutes. When used in excess, saponin is a rapid lytic agent, but will severely damage the leukocytes soon after stromatolysing the red blood cells.

In the examples which follow, the formulations can be adjusted to take into account certain general considerations.

Since commercial saponin is not a pure material, adjustments in the concentration may be needed for various lots of saponin powder supplied. Within limits, it is possible to change the concentration of saponin added to a given blood sample, if a compensating change in volume of the saponin reagent is also made. The saponin concentration in the lytic diluent ordinarily is within the range of 0.15% to 0.40% w/v. The amount of saponin present in the lysing reagent is 0.0020 to 0.0025 grams per 100 uL of whole blood.

When the blood sample is prediluted with a non-lytic diluent, the lytic reagent can contain a higher concentration of saponin, approximately 0.30% to 4.0%, and the alkaline buffer is best included in the prediluent. The volume of lytic reagent added to the prediluted blood is approximately 1 to 10 times that of the whole blood sample.

Preservatives can be added to the lytic diluent and the lytic reagent to inhibit the growth of microorganisms. Water soluble preservatives, such as methyl paraben, propyl paraben, formaldehyde, acetaldehyde, dimethylolurea, 2-pyridinethiol-1-oxide, sorbic acid, and potassium sorbate can be used. The sorbic acid can be added in the amount of 0.01% to 0.10% w/v to the lytic diluent.

Additives to the lysing reagent substantially can enhance the separation of the four main white blood cell clusters. The use of 2-phenoxyethanol in a range of 0.3 to 0.8% v/v gives enhanced histograms with most blood samples. Other related compounds, such as 1-phenyl-2-propanol, 2-phenyl-1-propanol, 3-phenoxy-1-propanol and 3-phenyl-1-propanol in the same concentration range result in a similar improvement to the white blood cell histogram. These additives also can include polyhydroxy compounds such as glucose, lactose, and sucrose, in the concentration range of 2 to 8%. Mixtures of more than one additive will give at times improved results. The lysing reagent contains alkali metal salts in a concentration range of 0.2% to 0.6% w/v.

The saponin lytic diluent is formulated for the parameters to be measured. For determinations of fluorescence, the saponin concentration is in the range of 0.15 to 0.25% w/v, the sodium chloride is in the range of 0.2 to 0.6% w/v, the volume of the lytic diluent being 6 to 15 times the volume of the whole blood sample, and a fluorescent dye is included as is discussed below.

Generally, cyanine dyes are employed which contain sulfonic acid side chains and which suitably fluoresce by excitation in the blue to green range 488 to 540 nm, or by excitation with red light of 630 to 640 nm, and which are sufficiently stable in aqueous solution.

Examples of such dyes are:

A. Cyanine dyes at a concentration of about $1 \times 10^{-6}$M to $5 \times 10^{-5}$M:

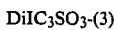

DiIC$_3$SO$_3$-(3)

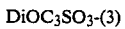

DiOC$_3$SO$_3$-(3)

DiSC$_3$SO$_3$-(3)

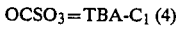

OCSO$_3$=TBA-C$_1$ (4)

and many others. These are usable with a He/Ar laser at 488 or 514 nm light.

By Cyanine dyes at an approximate concentration $1 \times 10^{-5}$M:

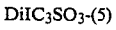

DiIC$_3$SO$_3$-(5)

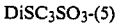

DiSC$_3$SO$_3$-(5)

These are usable with a He/Ne laser at 633 nm light.

C. Thiazine dyes, for example, sulforhodamine B.

The abbreviations for the dyes are those used by Alan Waggoner, Biochem 13 3315 (1974). He/Ar means Helium/Argon; whereas, He/Ne means Helium/Neon.

Glutaraldehyde is the preferred cross-linking fixing reagent. Other cross-linking dialdehydes include glyoxal, malonaldehyde, and the like. Unsaturated monoaldehydes, such as acrolein or methacrolein, likewise can be used. It is known that acrolein under certain conditions is a bifunctional cross-linking agent.

The preferred cross-linking reagent which is added to the lysed blood sample contain glutaraldehyde. The fixing reagent consists of glutaraldehyde in a concentration range of 0.5% to 4.0% v/v, an alkali metal chloride or sulfate in a concentration range of 0.2% to 0.8% w/v, and a buffer salt in a concentration range of 0.0% to 2.0% w/v, to maintain pH in the range of 7.0 to 8.0 in the treated blood. The volume of fixing reagent added to the lysed whole blood is in the range of 1 to 5 times that of the lysing reagent, so that the concentration of glutaraldehyde in the lysed and fixed blood solution is in the range of 0.20% to 2.0% v/v. The buffer can be sodium bicarbonate, phosphates, or Good's buffers, such as morpholinopropanesulfonic acid. If the pH of the reagent system is substantially below 7, there is a tendency for the lysed and fixed blood solution to gel. The pH is maintained within the range of 7.0 to 8.0 throughout the procedures. The osmolality generally falls within the range of 150 to 350 mOs/L.

A sodium chloride solution, which can contain potassium ferricyanide and potassium cyanide is needed to bring the concentration of cells to a suitable level for counting. The conductivity of the lysed and fixed blood solution is adjusted to be equal to that of the sheath fluid if a focused aperture is used. Potassium ferricyanide and potassium cyanide can be incorporated to convert the oxyhemoglobin to a suitable chromogen, and are incorporated in a range of 0.05 to 5% w/v and 0.01 to 0.2% w/v, respectively.

Heating of the lysed and fixed blood solution often is useful to accelerate the modification of the leukocytes and rapidly give stable clusters for flow analysis. Heating to about 60° to 75° C. for about 10 to 30 seconds prior to measurement is useful. Heating to 70° to 75° C. for about 10 seconds gives the best results. In manual preparations, it is convenient to immerse the blood solution, contained in a glass test tube, into a 70° to 75° C. water bath with swirling to achieve heating. In an automated system, heating can be accomplished with a coiled electrical resistance wire around the sample chamber, or by other suitable means.

EXAMPLE 1

White blood cell cytogram by fluorescence and light scatter using a COULTER® EPICS®V Flow Cytometer.

FORMULATIONS

Lytic diluent
  0.2% w/v saponin
  0.6% w/v sodium chloride
  1.0% Hepes Buffer
  Cyanine dye $1\times10^{-5}$M Di I-C$_3$SO$_3$-(3)
  adjust pH to 7.2 with sodium hydroxide.
Fixing reagent
  0.5% v/v glutaraldehyde
  1.5% w/v sodium bicarbonate To 0.6 ml of the lytic diluent in a test tube is added 50 uL of EDTA anticoagulated whole blood with swirling. As soon as the blood solution clears in about five to ten seconds, 2.0 ml of the fixing reagent is added with swirling. After fifteen seconds the mixture is heated in a 70° C. water bath for fifteen seconds with swirling.

Figure 1:
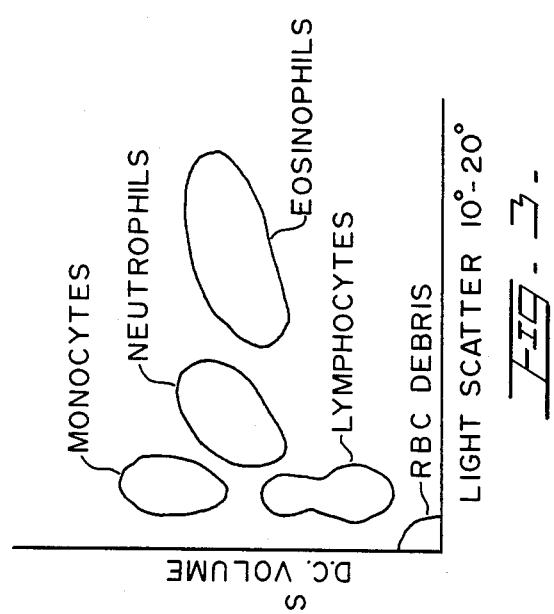

The preparation is analyzed on EPICS V Flow Cytometric System using 514 nm He/Ar laser light at 200 mwatt. A 540 nm interference filter and a 570 nm long pass filter are placed in the fluorescence channel. The white blood cell histogram is collected as fluorescence vs light scatter (2° to 20°), as shown in FIG. 1, or as fluorescence/light scatter vs light scatter.

Four distinct clusters of white blood cells are observed. Sorting of cells in each of these clusters and microscopic examination shows that the cells are lymphocytes at low light scatter-low fluorescence; monocytes at intermediate light scatter-intermediate fluorescence; neutrophils at a high light scatter-high fluorescence; and eosinophils at high light scatter-very high fluorescence. The dye strongly stains the eosoniphilic granules of eosinophils and neutrophils, and weakly stains the cytoplasm of all the white blood cells.

A fifth cluster, not illustrated, sometimes is observed at low light scatter-intermediate fluorescence.

EXAMPLE 2

White blood cell histogram by fluorescence and light scatter using a COULTER TPS-1 equipped with 30 mwatt HeNe laser at 633 nm.

FORMULATIONS

Lytic diluent
  0.2% w/v saponin
  0.5% w/v sodium sulfate
  3.0% w/v sucrose
  cyanine dye $1\times10^{-5}$M DiIC$_3$SO$_3$-(5)
Fixing reagent
  1.0% v/v glutaraldehyde
  0.8% w/v sodium chloride
  0.5% w/v sodium bicarbonate To 1.0 ml of the lytic diluent in a test tube is added with swirling 0.1 ml of whole blood anticoagulated with EDTA. As soon as the blood solution clears in about five to seven seconds, 2.0 ml of the fixing reagent is added with swirling. After fifteen seconds, the mixture is heated in a 60° C. to 70° C. water bath with swirling for thirty seconds. The preparation is analyzed by a COULTER TPS-1 Flow Cytometer equipped with a 30 mwatt HeNe laser. Forward light scatter is measured in an angular range of 2° to 20°. Fluorescence is measured using a 665 nm long pass filter.

Figure 2:
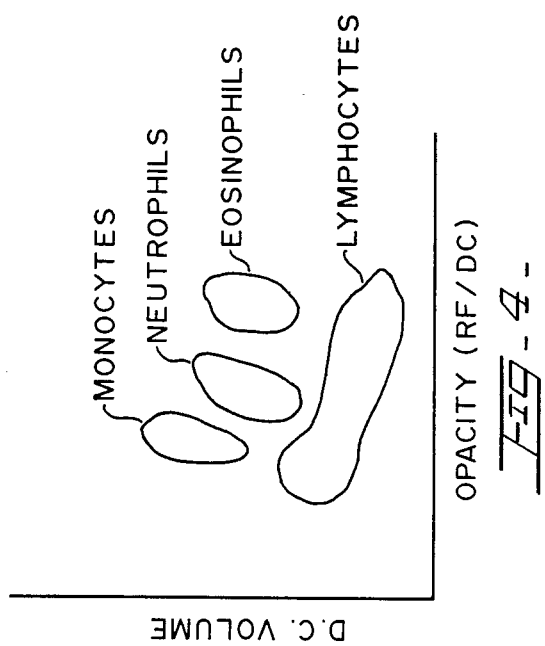

The cytogram is collected as fluorescence vs light scatter, as illustrated in FIG. 2, and shows four distinct clusters. The lymphocytes appear at low fluorescence-low light scatter; the monocytes at intermediate fluorescence-intermediate light scatter; the neutrophils appear at intermediate fluorescence-high light scatter; and the eosinophils at high fluorescence-high light scatter.

EXAMPLE 3

White blood cell histogram by light scatter vs DC volume using a square hole flow cytometer.

FORMULATIONS

Lytic diluent
  0.16% w/v saponin
  0.2% w/v sodium sulfate
  4.0% w/v sucrose
Fixing reagent
  1.5% v/v glutaraldehyde
  0.1% w/v sodium bicarbonate
  0.4% w/v sodium chloride To 1.5 ml of the lytic diluent in a test tube is added with swirling 0.1 ml whole blood anticoagulated with EDTA. As soon as the blood solution clears, in approximately five to seven seconds, 2.0 ml of the fixing reagent is added with swirling. The solution is brought to isoconductivity with respect to the sheath fluid by addition of a suitable volume of 1.6% w/v sodium chloride to the solution.

The prepration is analyzed by a COULTER type of flow cytometer containing a flow cell consisting of a COULTER aperture with a square cross section, allowing electro-optical measurements using a 1 mwatt HeNe laser. Forward light scatter, DC volume and RF size can be determined simultaneously with this device. A mask is used to block the narrow forward angle scattering, allowing light scatter to be collected in an approximate range of 10° to 20°, or 10° to 15°. White cell histograms are collected as light scatter vs DC volume, showing four distinct clusters, as illustrated in FIG. 3. Lymphocytes are seen at low light scatter-low volume; monocytes are seen at low light scatter-high volume; neutrophils are seen at intermediate light scatter-intermediate volume and eosinophils are present at high light scatter-intermediate volume.

The square hole flow cytometer and its uses are described more fully by R. A. Thomas, T. A. Yopp, B. D. Watson, D. H. K. Hindman, B. F. Cameron, S. B. Leif, B. C. Leif, L. Roque and W. Britt in the Journal of Histochemistry and Cytochemistry, Vol. 25, No. 77, pp. 827-835 (1977).

Cytograms also can be collected as light scatter/DC volume vs DC volume.

EXAMPLE 4

White blood cell histogram by opacity (RF size/DC volume) and DC volume using the square hole flow cell, HeNE laser.

FORMULATIONS

Lytic diluent
 0.4% w/v saponin
 0.2% w/v sodium chloride
 0.5% v/v 2-phenoxyethanol
 0.03% w/v methyl paraben preservative
Fixing reagent
 2.0% v/v glutaraldehyde
 0.4% w/v sodium chloride
 0.1% w/v sodium bicarbonate To 0.6 ml of lytic diluent in a test tube is added with swirling 0.10 ml whole blood anticoagulated with EDTA. After ten seconds, 1.0 ml of fixing reagent is added with swirling. The mixture is heated in a 70° C. water bath for fifteen seconds. The solution is brought to isoconductivity with the sheath fluid by addition of a suitable volume of 1.6% w/v sodium chloride.

Figure 4:
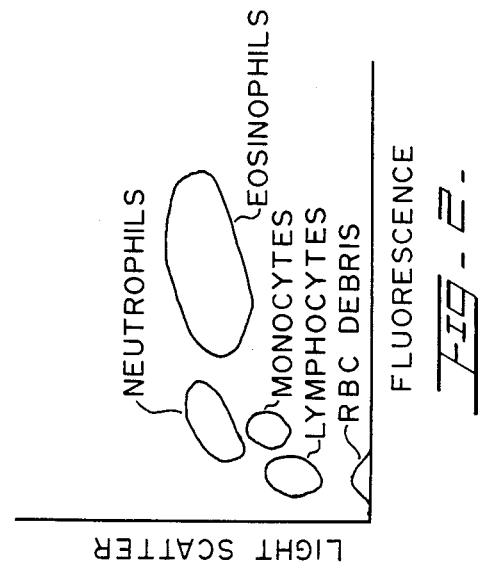

The preparation is analyzed by the instrument described in Example 3, measuring opacity vs DC volume. Four distinct clusters of white blood cells are found, as shown in FIG. 4. Lymphocytes appear at low to high opacity-low volume; monocytes are seen at low opacity-high volume; neutrophils are seen at intermediate opacity-high volume and eosinophils are seen at high opacity-high volume.

This procedure also gives good cytograms in the 10° to 20° light scatter vs DC volume parameters. The RF, DC and light scatter parameters can be collected simultaneously and used together by forming ratios, or by selective gating to give improved cluster definition.

EXAMPLE 5

White blood cell histogram by opacity (RF size/DC volume), vs DC volume using the focused square hole flow cell or an unfocused standard COULTER aperture. Demonstration of the predilution method.

FORMULATIONS

Prediluent
 0.3% w/v sodium chloride
 0.1% w/v sodium bicarbonate
Lytic reagent
 2.5% w/v saponin
 0.4w/v sodium chloride
 0.19.% w/v sorbic acid (preservative)
Fixing reagent
 2.0% v/v glutaraldehyde
 0.4% w/v sodium chloride To 1.0 ml of the prediluent is added with swirling 0.10 ml of whole blood, anticoagulated with EDTA, followed by 0.10 ml of the lytic reagent. After ten seconds, 1.0 ml of the fixing reagent is added with swirling, and the sample is heated in a 70° C. water bath for fifteen seconds. For use with a focused square hole aperture, the sample is diluted 1:1 with 0.9% w/v of sodium chloride and the conductivity is adjusted to be equal to that of the sheath fluid by suitable addition of 2.0% w/v of sodium chloride.

Figure 5:
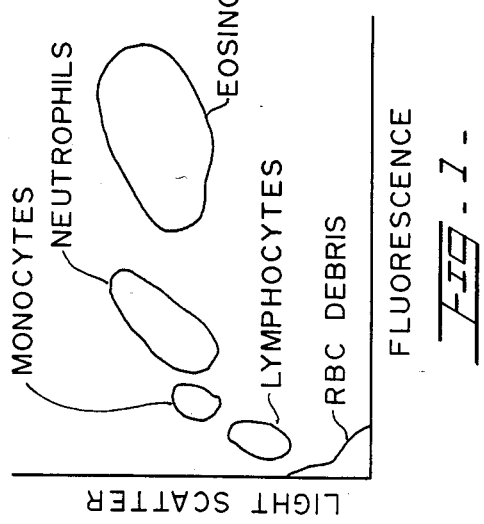

For use with an unfocused aperture in an aperture bath, the sample is diluted 10 times with isotonic diluent. No correction for conductivity is needed. Determination of the opacity (RF size/DC volume) vs DC volume gives four leukocyte clusters, as shown in FIG. 5. The lymphocytes appear at low to high opacity-low volume; monocytes and neutrophils are seen at intermediate opacity and high volume, as clearly separated populations; and eosinophils are located at high opacity and high volume.

EXAMPLE 6

White blood cell histogram by opacity (RF size/DC vol) vs DC volume parameters using a COULTER COUNTER Model S Plus, with mixing chamber and focused aperture adaptions. cl FORMULATIONS Prediluent
 0.3% w/v sodium chloride
 0.4% w/v sodium bicarbonate
Lytic reagent
 0.35% w/v saponin
 0.4% w/v sodium chloride
 0.1% w/v acetaldehyde preservative
Fixing reagent
 3.0% v/v glutaraldehyde
 0.4% w/v sodium chloride
Diluent
 4.0% w/v sodium chloride The instrument aspirates a whole blood sample anticoagulated with EDTA into the sampling loop, where 28 ul of blood is segmented. A 170 uL portion of the lytic reagent is delivered into the sample chamber, followed promptly by the whole blood sample carried by 150 uL of the prediluent. Mixing of the sample chamber by nutation is started and 100 uL of the lytic reagent is added immediately. After seven seconds lysing time a 250 uL portion of the fixing reagent is added. Heating is initiated immediately, bringing the sample to 70° C. in about seven seconds. After seven more seconds at this temperature 170 uL of the diluent is added for conductivity adjustment, the mixing is stopped, and the sample is fed into a focused flow cell for measurement of the DC volume and RF size parameters. After sampling, the bottom drain is opened and the excess sample is removed from the sample chamber, which is further rinsed in order to reduce "carry over", and to cool the sample chamber in preparation for the next sample.

Measurement of the DC volume and RF size parameters allow the discrimination of four leukocyte populations as described in the former examples and as shown in FIG. 5.

While in the foregoing specificaation, a detailed description of the invention has been set down for the purpose of illustration, many variations in the details herein given may be made by those skilled in the art without departing from the spirit and scope of the invention.

We claim:

1. A method for stromatolysing the red blood cells in a sample of whole blood and for classification of leukocytes into four categories, one of said categories being eosinophils, which comprises the steps of:
   I. treating a sample of whole blood with aqueous solutions of the following components:
      (A) a lysing reagent comprising
         (1) a single lytic diluent containing saponin, or
         (2) two solutions to be added separately to said sample of whole blood, consisting of
            (a) a prediluent and
            (b) a lytic reagent containing saponin; and then with
      (B) a fixing reagent containing a cross-linking compound; each of said components (A) and (B) being maintained at a predetermined concentration, pH and osmolality;
   II. measuring by instrumentation at least two of the primary parameters of DC volume, RF size, fluorescence, and light scatter, to produce cytograms; and
   III. observing four populations of leukocytes, one of said categories being eosinophils.

2. The method of claim 1 which further includes correlating the measured parameters of RF size/DC volume vs DC volume.

3. The method of claim 1 which further includes correlating the measured parameters of light scatter vs DC volume.

4. The method of claim 1 which further includes correlating the measured parameters of light scatter/DC volume vs DC volume.

5. The method of claim 1 which further includes correlating the measured parameters of fluorescence vs light scatter.

6. The method of claim 1 which further includes correlating of the measured parameters of fluoresence/light scatter vs light scatter.

7. The method of claim 1 wherein said categories of leukocytes are: lymphocytes, monocytes, neutrophils and eosinophils.

8. The method of claim 1 wherein the blood sample which has been treated as in step I is heated to an elevated temperature of about 60° to 75° C. for about 10 to 30 seconds prior to measurement by instrumentation as in step II.

* * * * *

UNITED STATES PATENT AND TRADEMARK OFFICE
CERTIFICATE OF CORRECTION

PATENT NO. : 4,751,179
DATED : June 14, 1988
INVENTOR(S) : Stephen L. Ledis et al.

It is certified that error appears in the above—identified patent and that said Letters Patent is hereby corrected as shown below:

Column 1, line 61, change "1967" to --1976--;
Column 2, line 9, change "where" to --when--;
Column 4, line 7, change "221" to --211--;
Column 5, line 42, change "agaibst" to --against--;
Column 6, line 52, change "By" to --B.--;
Column 9, line 3, change "prepration" to --preparation--;
Column 10, line 8, change "0.4w/v" to --0.4% w/v--;
Column 10, line 9, change "0.19%" to --0.1%--;
Column 10, line 54, change "ul" to --uL--;
Column 11, line 7, change "specificaation" to --specification--.

Signed and Sealed this

Twenty-third Day of July, 1991

Attest:

HARRY F. MANBECK, JR.

*Attesting Officer*    *Commissioner of Patents and Trademarks*